United States Patent
Zhou

(10) Patent No.: US 7,846,148 B2
(45) Date of Patent: Dec. 7, 2010

(54) CATHETER HAVING INCREASED CURVE PERFORMANCE THROUGH HEAT TREATMENT

(75) Inventor: Pu Zhou, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1057 days.

(21) Appl. No.: 09/957,361

(22) Filed: Sep. 20, 2001

(65) Prior Publication Data

US 2003/0055402 A1 Mar. 20, 2003

(51) Int. Cl.
*A61M 25/00* (2006.01)

(52) U.S. Cl. .................................... 604/523

(58) Field of Classification Search ........... 604/264, 604/164.01, 530, 531, 158, 239, 523; 264/632, 264/634, 635, 299, 479, 464, 896, 196

See application file for complete search history.

(56) References Cited

U.S. PATENT DOCUMENTS

| | | | |
|---|---|---|---|
| 4,292,270 A * | 9/1981 | Hannah et al. ............... 264/320 |
| 4,464,176 A | 8/1984 | Wijayarathna |
| 4,817,613 A | 4/1989 | Jaraczewski et al. |
| 4,886,506 A | 12/1989 | Lovgren et al. |
| 4,898,591 A | 2/1990 | Jang et al. |
| 5,047,045 A | 9/1991 | Arney et al. |
| 5,114,402 A | 5/1992 | McCoy |
| 5,156,594 A | 10/1992 | Keith |
| 5,290,229 A | 3/1994 | Paskar |
| 5,335,410 A | 8/1994 | Burnham |
| 5,477,856 A | 12/1995 | Lundquist |
| 5,674,208 A | 10/1997 | Berg et al. |
| 5,810,867 A | 9/1998 | Zarbatany et al. |
| 5,851,464 A * | 12/1998 | Davila et al. ................ 264/103 |
| 5,885,259 A | 3/1999 | Berg |
| 5,911,715 A | 6/1999 | Berg et al. |
| 6,030,360 A | 2/2000 | Biggs |
| 6,030,405 A * | 2/2000 | Zarbatany et al. ........... 606/191 |
| 6,042,578 A | 3/2000 | Dinh et al. |
| 6,146,355 A | 11/2000 | Biggs |
| 6,156,842 A * | 12/2000 | Hoenig et al. ............... 525/171 |
| 6,159,187 A * | 12/2000 | Park et al. ................... 604/264 |
| 6,171,295 B1 | 1/2001 | Garabedian et al. |
| 6,187,130 B1 | 2/2001 | Berard et al. |
| 6,212,422 B1 | 4/2001 | Berg et al. |
| 6,245,030 B1 | 6/2001 | DuBois et al. |

OTHER PUBLICATIONS

Jansen, "Nucleating Agents for Partly Crystalline Polymers," dated on or before Sep. 20, 2001, pp. 863-875.

* cited by examiner

*Primary Examiner*—Nicholas D Lucchesi
*Assistant Examiner*—Christopher D Koharski
(74) *Attorney, Agent, or Firm*—Crompton, Seager & Tufte, LLC

(57) ABSTRACT

The present invention includes catheters and catheter shafts having a curved portion, for example, a curved distal portion. The curved distal portion may be formed by subjecting the distal portion, which might include one or more polymeric segments or layers, to heat at or above the melt temperature thereof. Heating at or above the melt temperature may to reduce residual stress and eliminate heat history.

15 Claims, 1 Drawing Sheet

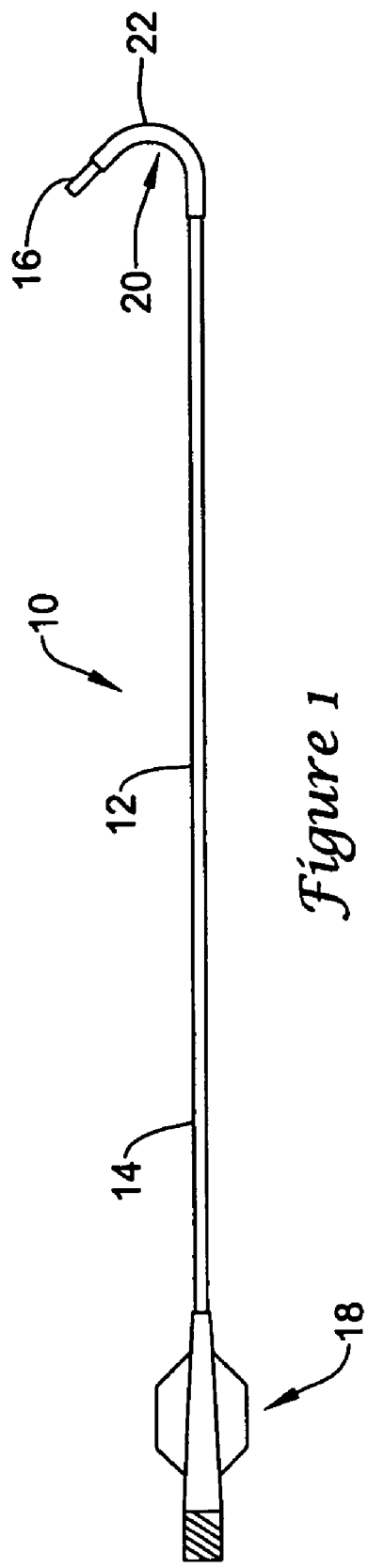
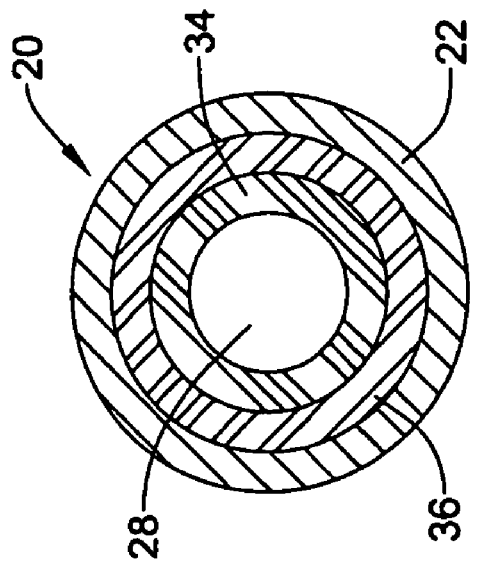
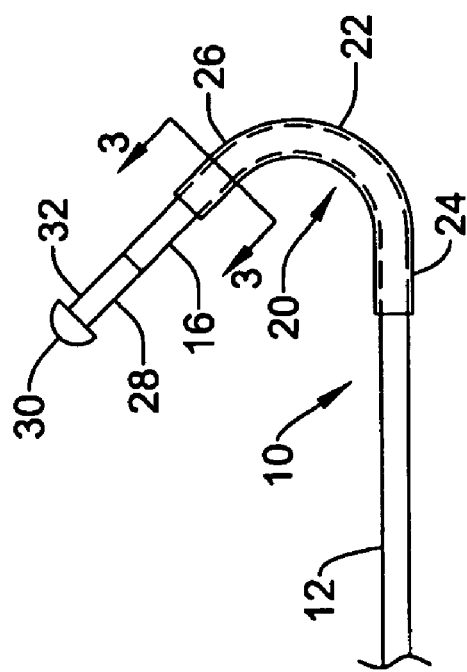

CATHETER HAVING INCREASED CURVE PERFORMANCE THROUGH HEAT TREATMENT

FIELD OF THE INVENTION

The present invention relates generally to catheters for performing medical procedures. More particularly, the present invention relates to intravascular catheters having a curved portion.

BACKGROUND OF THE INVENTION

A wide variety of intravascular catheters have been developed to diagnose and treat vascular diseases. Some types of catheters include a curved or shaped distal portion in order to facilitate navigation of the catheter through the vasculature. Formation of the curved portion usually comprises shaping and heat treating the distal end of the catheter below the melting point of the polymers contained therein, which may result in undesirable physical properties.

SUMMARY OF THE INVENTION

To reduce or eliminate such undesirable physical properties, the present invention provides design and manufacturing alternatives for catheters having a shaped or curved portion as described in more detail hereinafter.

BRIEF DESCRIPTION OF THE DRAWINGS

FIG. 1 is a plan view of a catheter including a shaped distal portion according to an embodiment of the invention, together with a retention sleeve;

FIG. 2 is an enlarged view of the shaped distal portion of the catheter shown in FIG. 1, together with a retention sleeve and a forming mandrel; and FIG. 3 is a cross-sectional view of FIG. 2 taken along line 3-3.

DETAILED DESCRIPTION OF THE PREFERRED EMBODIMENTS

The following description should be read with reference to the drawings wherein like reference numerals indicate like elements throughout the several views. The detailed description and drawings illustrate embodiments by way of example, not limitation.

FIG. 1 is a plan view of a catheter 10 comprising an elongate shaft 12 having a proximal end 14, a distal end 16, and a shaped distal portion 20. Shaped distal portion 20 includes at least one polymeric segment and/or layer which allows the distal portion 20 to be formed by shaping and heat treating it to a temperature above the melting point of one or more of the polymeric segment(s) and/or layer(s). It is believed that heat treating to temperatures above the melting point of the polymeric segment(s) or layer(s) of the distal portion 20 may eliminate heat history, residual stress, and morphological orientation and may restore the original physical properties of catheter 10. Such heat treating is not limited to the distal portion 20, but may be equally applicable to any portion of catheter 10, including shaped and straight portions, to eliminate heat history, residual stress, and morphological orientation.

As used herein, heat treating is understood to be mean a thermal process of exposing or generating heat in the polymeric segment(s) or layer(s). Heat treating may be accomplished by a number of methods and techniques. For example, heat treating may include exposure of the polymeric segment(s) or layer(s) of the distal portion 20 to infrared energy, radio frequency electromagnetic energy, radiant heating, laser energy, etc. Alternatively, the polymeric segment(s) or layer(s) of the distal portion 20 may be placed into an oven or a die that is coupled to a heat source. A person of ordinary skill in the art will be familiar with heat treating techniques appropriate for multiple embodiments of the invention.

Catheter 10 may comprise any one of multiple different catheter types. These catheter types include, but are not limited to, a guide catheter, a diagnostic catheter, a balloon catheter, an atherectomy catheter, etc. A person of ordinary skill in the art will be familiar with different types of catheters appropriate for multiple embodiments of the present invention. For purposes of illustration only, catheter 10 is depicted in FIG. 1 as a guide catheter.

A manifold 18 may be disposed at proximal end 14 of elongate shaft 12. Manifold 18 may comprise a single-port adapter (as shown) for a guide catheter, or a double-port adapter, a multi-port adapter, a connector, etc., depending on the type of catheter selected. A therapeutic or diagnostic device (not shown) such as an inflatable balloon or a rotating burr may be connected to distal end 16 of elongate shaft 12, depending on the type of catheter selected. The elongate shaft 12 may also incorporate one or more lumens and/or mechanisms necessary to operate such therapeutic and diagnostic devices.

Elongate shaft 12 may be generally tubular and may be manufactured from a number of materials including, but not limited to, polymers such as polyoxymethylene (POM), polybutylene terephthalate (PBT), polyether block ester available under the trade name ARNITEL, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, and perfluoro(propyl vinyl ether) (PFA); polymer/metal composites including any of the polymers described above in combination with a metallic reinforcement such as a coil or braid formed of stainless steel, nickel alloy, or nickel-titanium alloy; and combinations thereof. Elongate shaft 12 may be manufactured so as to maintain a level of flexibility and torquability appropriate for maneuvering catheter 10 through the vasculature. For example, shaped portion 20 may comprise a polymer/metal composite having an inner lubricious polymer layer (e.g., PTFE), an intermediate reinforcement layer (e.g., SST braid), and an outer polymeric layer (e.g., PEBA) to facilitate thermal processing as described in more detail below.

The shaped distal portion 20 is conventionally included to aid in the advancement of catheter 10 through the vasculature. For example, the shaped distal portion 20 may aid navigation of the catheter 10 over the aortic arch to access a coronary artery. The shaped distal portion 20 is typically formed by shaping and holding the catheter 10 in a configuration having a curve near distal end 16 and then heat treating catheter 10 to a temperature below the melting point of all polymers contained in the shaft 12.

Such shaping and heat treating of the catheter 10, followed by cooling thereof, imparts and maintains the shape or curve of the distal portion 20. However, such shaping and heat treating catheters may also lead to changes in the physical properties of catheter 10. For example, shaping and heating may increase the residual stress, alter the morphological orientation of particles within elongate shaft 12, and/or alter stiffness of elongate shaft 12. Changes in these and other physical properties may compromise the intended physical characteristics contemplated during the design of catheter 10.

It is therefore desirable, in some cases, to restore the virgin or original characteristics of the polymeric materials contained within the shaped distal portion 20 or other portions of the elongate shaft 12. Although annealing, tempering, or other similar thermal processing techniques may be utilized to alleviate a limited amount of residual stress and restore to a limited degree the original morphological orientation, such techniques only heat the polymeric materials to a temperature below the melting point thereof, which may not completely accomplish the objective. Thus, heat treating the distal portion 20 or any other portion of the shaft 12 to a temperature below the melting point of the polymers contained therein may be sub-optimal and may compromise the intended performance of the catheter 10.

To avoid such a compromise, the present invention provides design and manufacturing alternatives for constructing catheter 10 having a distal shaped portion 20 that is formed by thermal processing above or equal to the melting temperature of the polymers contained therein.

For example, if the polymer(s) of the distal portion 20 comprise a blend of 10% ARNITEL brand polyether block ester and 90% PBT, the distal portion 20 may be heated to a temperature of 480 F for 2 minutes to have the desired effect. Also by way of example, if the polymer(s) of the distal portion 20 comprise DELRINE brand POM, the distal portion 20 may be heated to a temperature of 400 F for 4 minutes to have the desired effect.

Because heat treating the shaped distal portion 20 involves raising the temperature of the polymers contained therein to a point greater than or equal to the melting point thereof, it may be desirable to utilize a retention sleeve 22 during the thermal processing. The retention sleeve functions to maintain the outer shape and structure of the distal portion 20 and to prevent the molten polymers from flowing. The sleeve 22 may extend over all or a portion of the elongate shaft 12, depending on the length of the shaft 12 exposed to the heat. After thermal processing and cooling, the sleeve 22 may be removed or left thereon to reduce polymeric creep (i.e., to retain the shape of the distal portion 20).

As mentioned above, one of the purposes for including sleeve 22 is to maintain the shape and structure of elongate shaft 12 during heating. Because the temperature of elongate shaft 12 may equal or exceed the melting point of the polymers contained therein, molten polymeric portions of elongate shaft 12 may flow and cause unwanted deformation. The sleeve 22, thus, provides a physical barrier for preventing molten or partially molten portions of elongate shaft 12 from flowing away from their intended position and thus preserves the shape and structure of the outside surface of catheter 10. To better serve this function, the sleeve 22 may have a melting temperature that is greater than that of the polymeric materials of elongate shaft 12 being heat treated. The sleeve 22 may comprise, for example, a heat shrink tube made of fluorinated ethylene propylene.

FIG. 2 is an enlarged view of the shaped distal portion 20, together with the sleeve 22 and a mandrel 28. The mandrel 28 may be disposed within the elongate shaft 12 (e.g., within a lumen of elongate shaft 12) to extend through the distal portion 20 and/or other portions of the shaft 12 subject to heat treatment. As with the sleeve 22, the mandrel 28 provides a physical barrier to prevent molten or partially molten portions of elongate shaft 12 from flowing away from their intended position and thus preserves the shape and structure of the inside surface of catheter 10. The combination of the sleeve 22 and the mandrel 28 provide barriers for both the inside surface and the outside surface of the portion(s) of the elongate shaft 12 subject to heat treatment.

FIG. 3 is a cross-sectional view of FIG. 2 taken along line 3-3. In this illustration, the shaped distal portion 20 of the catheter shaft is disposed over the mandrel 28. The catheter shaft includes an inner polymeric layer 34 having a melt temperature and an outer polymeric layer 36 having a different melt temperature. Sleeve 22 is also seen. The shaped distal portion 20 can be subjected to heat that is at or above the melt temperature of the inner polymeric layer 34. The shaped distal portion 20 can be subjected to heat that is at or above melt temperature of the outer polymeric layer 36. The shaped distal portion 20 can be subjected to heat that is at or above the melt temperature of the inner polymer layer 34 and that is at or above the melt temperature of the outer polymeric layer 36.

As mentioned previously, the entire shaft 12 may be subject to heat treatment, or the heat treating process may be localized to a portion of elongate shaft 12. For example, heat exposure or generation may occur only along portions of elongate shaft 12 where the sleeve 22 is disposed thereon. In other words, the heat treatment zone may be limited to the region between the proximal 24 and distal 26 ends of the sleeve 22. When utilizing localized heat treatment, the unheated portions of the shaft 12 serve to limit molten polymer flow at the respective ends of the heat treatment zone.

For example, the heat treatment zone may be limited to a region between the proximal end 24 and distal end 26 of the sleeve 22. In this scenario, the length of the elongate shaft 12 not covered by the sleeve 22 would not be subject to heat treating, and thus would not be molten. These non-molten sections of elongate shaft 12 serve as a barrier for preserving the shape and structure of elongate shaft 12 at the ends of the heat treatment zone. When the sleeve 22 and the mandrel 28 are used in this scenario, essentially all sides of elongate shaft 12 subject to heat would have structural support during heat treatment.

If the entire length of the shaft 12 were exposed to heat, or if localized heat were applied to the distal end 16 of the shaft 12, there would not be a non-molten portion of the shaft 12 at the distal end of the heat treatment zone. In this scenario, a cap 30 coupled to a distal end 32 of the mandrel 28 may be used to prevent the flow of molten polymeric material at the distal extremity 16. In this embodiment, the cap 30 may abut the distal end 16 of elongate shaft 12 and the distal end 26 of the sleeve 22 to provide structural support. Alternatively, the sleeve 22 may incorporate an inward facing flange at the distal end 26 thereof to serve the same function. Those skilled in the art will recognize alternative designs and arrangements to accomplish the same function.

It should be understood that this disclosure is, in many respects, only illustrative. Changes may be made in details, particularly in matters of shape, size, arrangement of parts and order of steps without departing from the scope of the invention. The invention's scope is, of course, defined in the language in which the appended claims are expressed.

What is claimed is:

1. An intravascular catheter, comprising:
    an elongate shaft including a polymer having a melt temperature, the elongate shaft having a proximal end, a distal end and a lumen extending therethrough from the proximal end to the distal end;
    wherein the elongate shaft further includes a portion having a curve shape generally free of a residual stress as a result of being subjected to heat at or above the melt temperature, the residual stress being imparted in the curve shaped portion during curve formation.

2. The intravascular catheter of claim 1, wherein the curve shaped portion is proximal the distal end of the elongate shaft.

3. The intravascular catheter of claim 1, wherein the curve shaped portion includes an inner polymeric layer having a melt temperature and an outer polymeric layer having a different melt temperature, and wherein the inner polymeric layer of the curve shaped portion is generally free of the residual stress as a result of being subjected to heat at or above the melt temperature of the inner polymeric layer.

4. The intravascular catheter of claim 1, wherein the curve shaped portion includes an inner polymeric layer having a melt temperature and an outer polymeric layer having a different melt temperature, and wherein the outer polymeric layer of the curve shaped portion is generally free of the residual stress as a result of being subjected to heat at or above the melt temperature of the outer polymeric layer.

5. The intravascular catheter of claim 1, wherein the curve shaped portion includes an inner polymeric layer having a melt temperature and an outer polymeric layer having a different melt temperature, and wherein both the inner and outer polymeric layers of the curve shaped portion are generally free of the residual stress as a result of being subjected to hear at or above the melt temperatures of both the inner and outer polymeric layers.

6. The intravascular catheter of claim 1, wherein the curve shaped portion has an outer surface, and wherein a sleeve is disposed about the outer surface of the curve shaped portion while being subjected to heat at or above the melt temperature.

7. The intravascular catheter of claim 6, wherein the sleeve has a melt temperature greater than the melt temperature of the polymer.

8. The intravascular catheter of claim 1, wherein a mandrel is disposed within the lumen of the curve shaped portion while being subjected to heat at or above the melt temperature.

9. The intravascular catheter of claim 8, wherein the distal end of the elongate shaft has a distal end surface, and wherein the mandrel includes a cap abutting the distal end surface while the curve shaped portion is being subjected to heat at or above the melt temperature.

10. An intravascular catheter, comprising;
an elongate shaft having a proximal end, a distal end and a lumen extending therethrough from the proximal end to the distal end, the elongate shaft further including a curve shaped portion including a polymeric layer having a melt temperature;
wherein the polymeric layer of the curve shaped portion is generally free of a residual stress, wherein the polymeric layer of the curve shaped portion is bestowed with the residual stress during curve formation, but the polymeric layer of the curve shaped portion is generally free of the residual stress as a result of being subjected to heat at or above the melt temperature.

11. The intravascular catheter of claim 10, wherein the curve shaped portion is proximal the distal end of the elongate shaft.

12. The intravascular catheter of claim 10, wherein the polymeric layer is an inner polymeric layer, and wherein the curve shaped portion includes an outer polymeric layer.

13. The intravascular catheter of claim 10, wherein the polymeric layer is an outer polymeric layer, and wherein the curve shaped portion includes an inner polymeric layer.

14. The intravascular catheter of claim 10, wherein the polymeric layer is a multi-layer polymeric layer.

15. An intravascular catheter, comprising:
an elongate shaft including a polymeric layer having a melt temperature, the elongate shaft having a proximal end, a distal end and a lumen extending therethrough from the proximal end to the distal end; and
the elongate shaft further including a curve shaped portion proximal the distal end, wherein the curve shaped portion is generally free of residual stress as a result of being subjected to heat at or above the melt temperature, the residual stress bestowed in the polymeric layer during curve formation.

* * * * *